United States Patent
Halmann et al.

(10) Patent No.: US 11,559,280 B2
(45) Date of Patent: Jan. 24, 2023

(54) ULTRASOUND IMAGING SYSTEM AND METHOD FOR DETERMINING ACOUSTIC CONTACT

(71) Applicant: GE Precision Healthcare LLC, Wauwatosa, WI (US)

(72) Inventors: Menachem Halmann, Monona, WI (US); Cynthia A Owen, Powhatan, AR (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 123 days.

(21) Appl. No.: 16/870,667

(22) Filed: May 8, 2020

(65) Prior Publication Data

US 2021/0349211 A1    Nov. 11, 2021

(51) Int. Cl.
  *A61B 8/00*     (2006.01)
  *A61B 8/08*     (2006.01)

(52) U.S. Cl.
  CPC .............. *A61B 8/429* (2013.01); *A61B 8/463* (2013.01); *A61B 8/5253* (2013.01)

(58) Field of Classification Search
  CPC ....... A61B 8/429; A61B 8/444; A61B 8/5207; G01S 15/89; G01S 7/5208
  See application file for complete search history.

(56) References Cited

U.S. PATENT DOCUMENTS

| | | | |
|---|---|---|---|
| 3,002,704 A | 10/1961 | Grossfeld | |
| 5,485,841 A * | 1/1996 | Watkin | A61B 8/08 600/437 |
| 6,328,693 B1 * | 12/2001 | Miyatake | A61B 8/5238 600/443 |
| 10,192,032 B2 | 1/2019 | Himsl | |
| 2006/0058651 A1 * | 3/2006 | Chiao | A61B 8/483 600/437 |
| 2006/0178579 A1 * | 8/2006 | Haynes | G01G 23/3735 600/437 |
| 2007/0010742 A1 * | 1/2007 | Torp | A61B 5/6843 600/437 |
| 2009/0306514 A1 | 12/2009 | Imamura | |

(Continued)

OTHER PUBLICATIONS

"Confidence-Driven Control of an Ultrasound Probe" Pierre Chatelain, Alexandre Krupa, Nassir Navab. Confidence-Driven Control of an Ultrasound Probe. IEEE Transactions on Robotics, Institute of Electrical and Electronics Engineers (IEEE), 2017, 33 (6), pp. 1410-1424. hal-01551431.

*Primary Examiner* — Katherine L Fernandez
*Assistant Examiner* — Brooke Lyn Klein

(57) ABSTRACT

An ultrasound imaging system and method includes acquiring ultrasound image data of an object while translating the ultrasound probe, where the ultrasound probe includes a scanning surface. The ultrasound imaging system and method includes displaying an acquisition view during the process of acquiring the panoramic ultrasound data. The ultrasound imaging system and method includes automatically determining acoustic contact of the scanning surface with the object while acquiring the panoramic ultrasound data and displaying a color-coded indicator at the same time as the acquisition view, where the color-coded indicator represents the acoustic contact of the scanning surface in real-time during the process of acquiring the panoramic ultrasound data.

13 Claims, 13 Drawing Sheets

(56) References Cited

U.S. PATENT DOCUMENTS

| | | | |
|---|---|---|---|
| 2010/0185090 A1* | 7/2010 | Suzuki | G01S 15/8906 |
| | | | 600/443 |
| 2011/0096958 A1* | 4/2011 | Fukumoto | A61B 8/08 |
| | | | 382/106 |
| 2014/0031687 A1* | 1/2014 | Kurita | A61B 8/5253 |
| | | | 600/440 |
| 2014/0031688 A1 | 1/2014 | Perrey | |
| 2014/0058264 A1* | 2/2014 | Baym | A61B 8/429 |
| | | | 600/447 |
| 2015/0116361 A1 | 4/2015 | Braun | |
| 2016/0335742 A1* | 11/2016 | Yim | A61B 8/5253 |
| 2018/0078170 A1* | 3/2018 | Panescu | A61B 34/20 |
| 2018/0168546 A1* | 6/2018 | Ebata | A61B 8/5215 |
| 2018/0310920 A1 | 11/2018 | Specht | |
| 2019/0125298 A1 | 5/2019 | Abolmaesumi | |
| 2019/0328361 A1 | 10/2019 | Halmann | |
| 2019/0343490 A1* | 11/2019 | White | A61B 8/5223 |
| 2020/0077976 A1* | 3/2020 | Hirai | A61B 8/58 |

\* cited by examiner

ULTRASOUND IMAGING SYSTEM AND METHOD FOR DETERMINING ACOUSTIC CONTACT

FIELD OF THE INVENTION

The subject matter disclosed herein relates generally to a method and ultrasound imaging system for determining acoustic contact of an ultrasound probe during the acquisition of panoramic ultrasound data.

BACKGROUND OF THE INVENTION

Ultrasound imaging is an imaging modality capable of acquiring ultrasound data that may be viewed in real-time or stored and reviewed at times subsequent to the acquisition. During the acquisition of ultrasound data, it is important to have acoustic contact between the ultrasound probe and the object being scanned. The two biggest contributors to poor acoustic contact are having an inadequate amount of coupling gel on the ultrasound probe and having too little pressure while scanning. Poor acoustic contact while acquiring ultrasound data will result in ultrasound images with artifacts and/or regions that are missing in the resulting ultrasound images.

Experienced clinicians are more likely to maintain acoustic contact while acquiring ultrasound data, but even experienced clinicians may have trouble maintaining acoustic contact during more-involved procedures, such as acquiring panoramic ultrasound data wile translating the ultrasound probe. After acquiring panoramic ultrasound data, the ultrasound imaging system displays the panoramic ultrasound data as a panoramic view comprising a plurality of videos. If any portions of the panoramic ultrasound data were acquired with poor acoustic contact, the videos in the panoramic view will contain artifacts. Displaying a panoramic view based on panoramic ultrasound data including artifacts is distracting to the clinician and may make it difficult or impossible to make an accurate diagnosis based on the panoramic view. For at least these reasons, there is a need for an improved ultrasound imaging system and method for determining and indicating acoustic contact while acquiring panoramic ultrasound data.

BRIEF DESCRIPTION OF THE INVENTION

In one embodiment, a method of ultrasound imaging includes acquiring panoramic ultrasound data of an object while translating the ultrasound probe, wherein the ultrasound probe includes a scanning surface. The method includes displaying an acquisition view during the process of acquiring the panoramic ultrasound data. The method includes automatically determining acoustic contact of the scanning surface with the object while acquiring the panoramic ultrasound data. The method includes displaying a color-coded indicator at the same time as the acquisition view, where the color-coded indicator represents the acoustic contact of the scanning surface in real-time during the process of acquiring the panoramic ultrasound data.

In one embodiment, an ultrasound imaging system includes a display device, an ultrasound probe configured to acquire panoramic ultrasound data, wherein the ultrasound probe includes a scanning surface. The ultrasound imaging system includes a processor in electronic communication with the ultrasound probe and the display device. The processor is configured to control the ultrasound probe to acquire panoramic ultrasound data of an object while the ultrasound probe is translated. The processor is configured to display an acquisition view on the display device while the ultrasound probe is acquiring the panoramic ultrasound data. The processor is configured to display a color-coded indicator at the same time as the acquisition view, where the color-coded indicator represents the acoustic contact of the scanning surface in real-time while acquiring the panoramic ultrasound data.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION OF THE INVENTION

Figure 1:
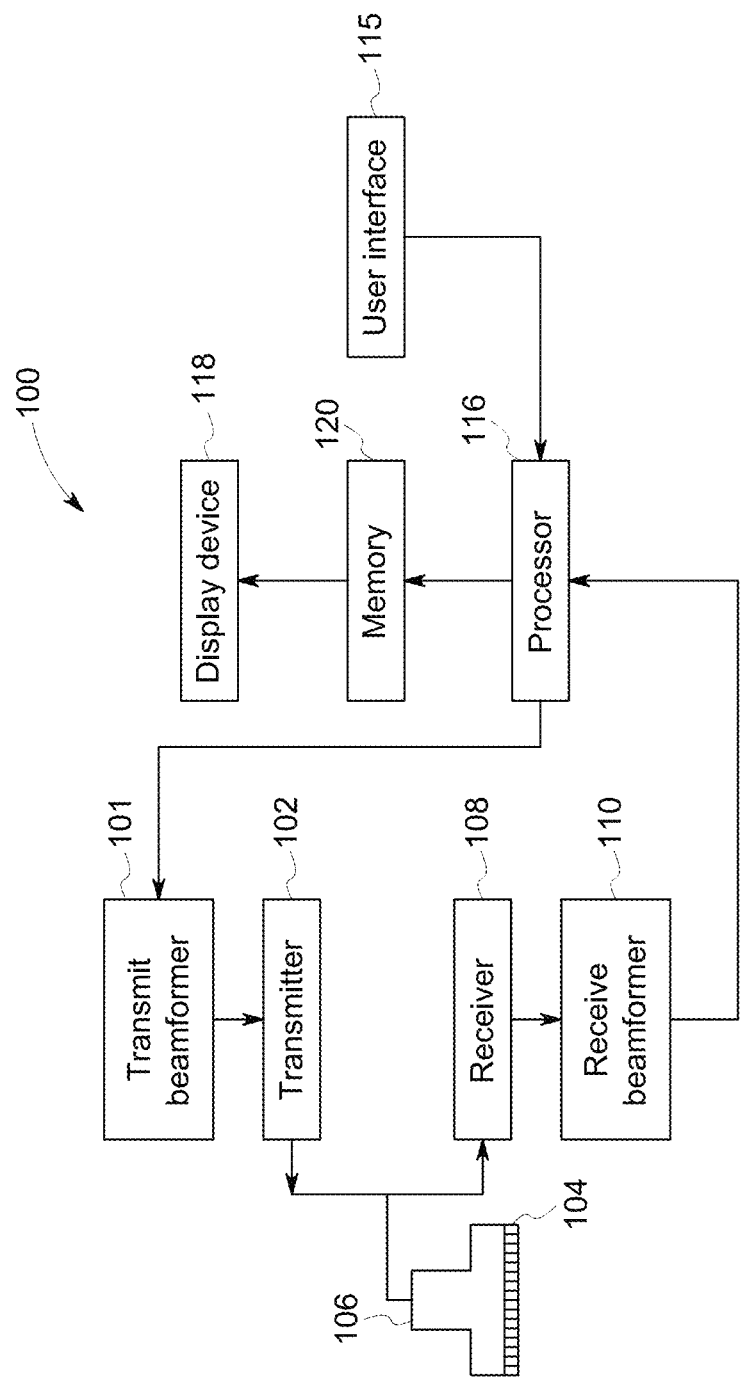
FIG. 1 is a schematic diagram of an ultrasound imaging system in accordance with an embodiment.

FIG. 1 is a schematic diagram of an ultrasound imaging system 100 in accordance with one embodiment of the inventive subject matter described herein. The ultrasound imaging system 100 includes a transmit beamformer 101 and a transmitter 102 that drive elements 104 within an ultrasound probe 106 to emit pulsed ultrasonic signals into an object or patient. According to an embodiment, the ultrasound probe 106 may be a linear probe, a curvilinear probe, a phased array probe, a linear phased array probe, a curvilinear phased array probe, a two-dimensional matrix array probe, a curved two-dimensional matrix array probe, a mechanical 3D probe, or any other type of ultrasound probe capable of being used to acquire panoramic ultrasound data.

The pulsed ultrasonic signals are reflected or back-scattered from structures in the body, such as blood cells or muscular tissue, to produce echoes that return to the elements 104. The echoes are converted into electrical signals by the elements 104, and the electrical signals are received by a receiver 108. The electrical signals representing the received echoes are passed through a receive beamformer 110 that outputs ultrasound data. The ultrasound probe 106 may contain electronic circuitry to do all or part of the transmit and/or the receive beamforming. For example, all or part of the transmit beamformer 101, the transmitter 102, the receiver 108, and the receive beamformer 110 may be situated within the ultrasound probe 106 in other embodiments. Scanning may include acquiring data through the process of transmitting and receiving ultrasonic signals. Ultrasound data acquired by the ultrasound probe 106 can include one or more datasets acquired with the ultrasound imaging system 100. A user interface 115 may be used to control operation of the ultrasound imaging system 100, including, to control the input of data, to change a scanning or display parameter, and the like. The user interface may include, for instance, one or more of a touchscreen, a keyboard, a touch pad, a track ball, a mouse, one or more rotary knobs, one or more hard keys, and one or more soft keys.

The ultrasound imaging system 100 also includes a processor 116 that controls the transmit beamformer 101, the transmitter 102, the receiver 108, and the receive beamformer 110. The processor 116 is in electronic communication with the probe 106 via one or more wired and/or wireless connections. The processor 116 may control the ultrasound probe 106 to acquire ultrasound data. The processor 116 controls which of the elements 104 are active and the shape of a beam emitted from the ultrasound probe 106. The processor 116 is also in electronic communication with a display device 118, and the processor 116 may process the data into images for display on the display device 118. The processor 116 may include one or more central processors according to an embodiment. According to other embodiments, the processor 116 may include one or more other electronic components capable of carrying out processing functions, such as one or more digital signal processors, field-programmable gate arrays, graphic boards, and/or integrated circuits. According to other embodiments, the processor 116 may include multiple electronic components capable of carrying out processing functions. Other embodiments may use two or more separate processors to perform the functions performed by the processor 116 according to the exemplary embodiment shown in FIG. 1. According to another embodiment, the processor 116 may also include a complex demodulator (not shown) that demodulates the radio frequency data and generates raw data. In another embodiment, the demodulation can be carried out earlier in the processing chain.

The processor 116 is adapted to perform one or more processing operations according to a plurality of selectable ultrasound modalities on the ultrasound data. The ultrasound data may be processed in real-time during a scanning session as the echo signals are received, such as by processing the ultrasound data without any intentional delay, or processing the ultrasound data while additional ultrasound data is being acquired during the same imaging session of the same person.

The data may be stored temporarily in a buffer (not shown) during a scanning session and processed in less than real-time in a live or off-line operation. Some embodiments of the inventive subject matter may include multiple processors (not shown) to handle the processing tasks that are handled by the processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire ultrasound data at a frame-rate of, for example, 10 to 30 hertz. Images generated from the data may be refreshed at a similar frame-rate. Other embodiments may acquire and display ultrasound data at different rates. For example, some embodiments may acquire ultrasound data at a frame-rate of less than 10 hertz or greater than 30 hertz.

A memory 120 is included for storing processed frames of acquired data. In one embodiment, the memory 120 is of sufficient capacity to store at least several seconds worth of ultrasound image data. The frames of data are stored in a manner to facilitate retrieval thereof according to their order or time of acquisition. The memory 120 may comprise any known data storage medium, such as one or more tangible and non-transitory computer-readable storage media (e.g., one or more computer hard drives, disk drives, universal serial bus drives, solid-state drives, or the like).

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form two- or three-dimensional image data. For example, one or more modules may generate B-mode, color Doppler, M-mode, color M-mode, spectral Doppler, Elastography, TVI, strain, strain rate and combinations thereof, and the like. Timing information indicating a time at which the data was acquired in memory may be recorded. The modules may include, for example, a scan conversion module to perform scan conversion operations to convert the image volumes from beam space coordinates to display space coordinates. A video processor module may read the image frames from a memory and displays an image in real time while a procedure is being carried out on a person. A video processor module may store the images in an image memory, from which the images are read and displayed.

Figure 2:
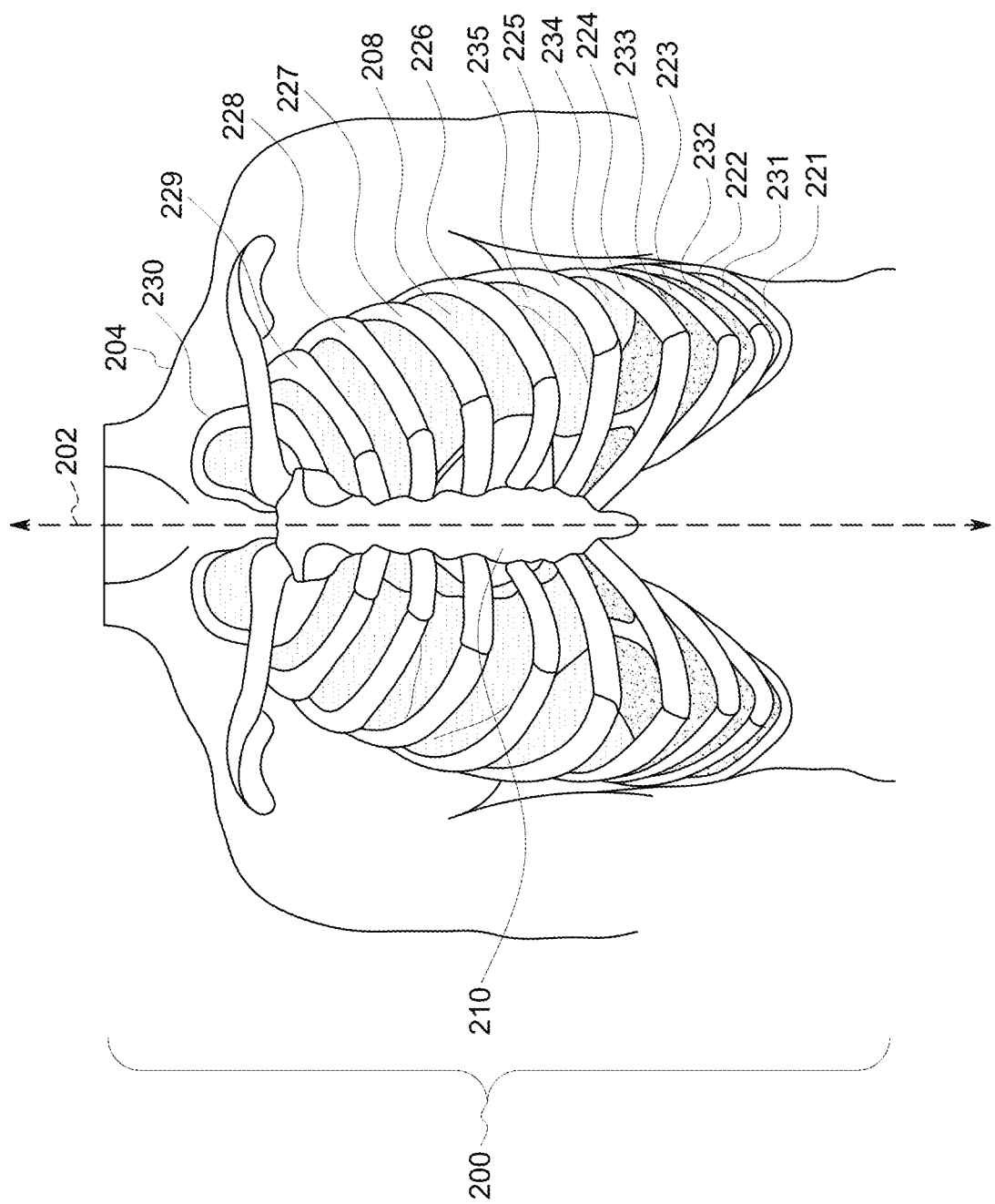
FIG. 2 illustrates a thoracic cavity according to an example.

FIG. 2 illustrates a thoracic cavity 200 of a person 204 according to one example. The ultrasound image data that is acquired (as described herein) may represent portions of the thoracic cavity 200, including lungs 208, a plurality of ribs, and a sternum 210 of the person 204. The plurality of ribs may include a first rib 221, a second rib 222, a third rib 223, a fourth rib 224, a fifth rib 225, a sixth rib 226, a seventh rib 227, an eighth rib 228, a ninth rib 229, and a tenth rib 230. FIG. 2 also shows a plurality of intercostal spaces located between the ribs. For instance, a first intercostal space 231, a second intercostal space 232, a third intercostal space 233, a fourth intercostal space 234, and a fifth intercostal space 235 are all represented in FIG. 2. The first intercostal space 231 is located between the first rib 221 and the second rib 222; the second intercostal space 232 is located between the second rib 222 and the third rib 223; the third intercostal space 233 is located between the third rib 223 and the fourth rib 224; and the fourth intercostal space 234 is located between the fourth rib 224 and the fifth rib 225. The thoracic cavity 200 of the person 204 includes additional intercostal spaces; however, these additional intercostal spaces have not been specifically identified on FIG. 2. In obtaining the ultrasound image data, the ultrasound probe 106 shown in FIG. 1 may be held in contact with an exterior surface of the skin of the person 204 and moved longitudinally along the person 204 (e.g., in a direction that is closer to parallel to the length or height of the person 204 than one or more other directions). This movement also causes the ultrasound probe 106 to move transversely relative to the plurality of ribs. For example, the ultrasound probe 106 may be moved in a direction that is parallel or substantially parallel to the sagittal plane 202 of the person 204 (e.g., within ten degrees of parallel, within 15 degrees of parallel, etc.). As the ultrasound probe 106 is moved in this direction during acquisition of ultrasound image data, the ultrasound probe 106 moves transversely or substantially transversely to directions in which the ribs are elongated.

Figure 3:
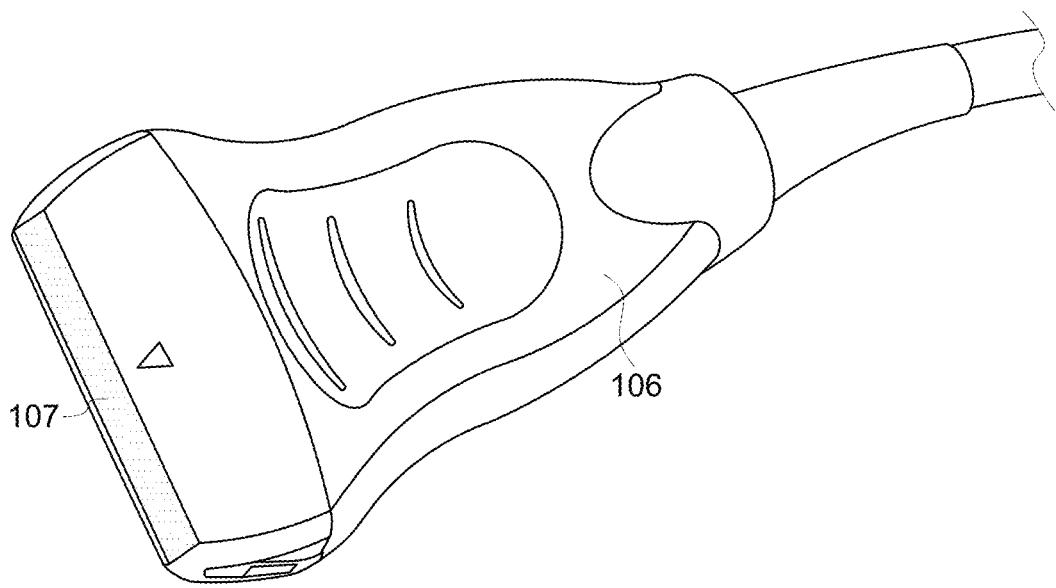
FIG. 3 illustrates an ultrasound probe according to an embodiment.
Figure 4:
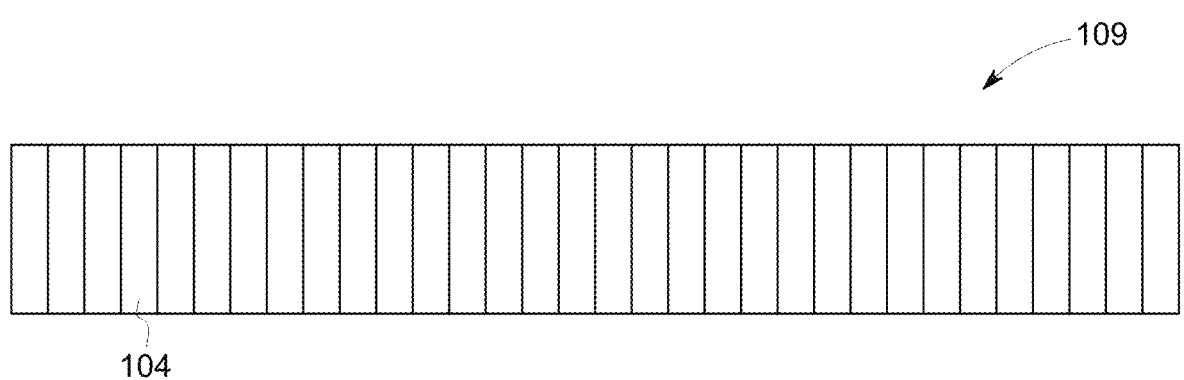
FIG. 4 illustrates a transducer array according to an embodiment.

FIG. 3 illustrates the ultrasound probe 106 in accordance with an embodiment. The ultrasound probe 106 includes a scanning surface 107 that is configured to be in contact with the patient or object being scanned. There scanning surface 107 may be an acoustic lens according to some embodiments. FIG. 4 is a schematic representation of a transducer array 109 according to an embodiment. A transducer array, such as the transducer array 109, is positioned beneath the scanning surface 109. The ultrasound probe 106 may include one or more matching layer positioned between the transducer array 109 and the scanning surface 107. For the best performance, the entire scanning surface 107 of the ultrasound probe 106 should be in acoustic contact with the patient or object being scanned.

The transducer array 107 shown in FIG. 4 shows 32 elements 104 arranged in a linear array in FIG. 4 for illustrative purposes. Ultrasound probes may include transducer arrays with different numbers of elements according to various embodiments. For example, linear array with 128 elements or 256 elements are commonly used. It is to be understood that ultrasound probes may include arrays with any number of elements. Additionally, FIG. 4 illustrates elements 104 arranged a linear array. Other embodiments may have the elements arranged in transducer arrays with different configurations including a 1.25D array, a 1.5D array, a 1.75D array, a 2D array, a curved array, or a convex array.

Figure 5:
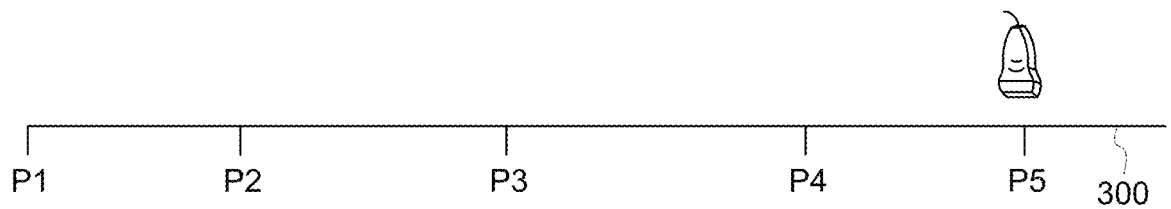
FIG. 5 illustrates a translation path according to an embodiment.

FIG. 5 is a schematic representation of a translation path 300 of the ultrasound probe 106 that may be used to acquire panoramic ultrasound data according to an exemplary embodiment. FIG. 5 shows the position of the ultrasound probe 106 at different times during the translation. For example, five specific positions are indicated on FIG. 4: P1, P2, P3, P4, and P5. Each of the positions (P1, P2, P3, P4, and P5) represents the position of the ultrasound probe 106 at a different time during the translation. For example, the ultrasound probe 106 is at position P1 at time T1; the ultrasound probe 106 is at position P2 at time T2; the ultrasound probe 106 is at position P3 at time T3; the ultrasound probe 106 is at position P4 at time T4; and the ultrasound probe 106 is at position P5 at time T5. It should be appreciated that the positions (P1, P2, P3, P4, and P5) represent just a subset of the ultrasound probe positions during the translation. It is expected that the clinician may smoothly translate the ultrasound probe 106 along the translation path 300. According to an embodiment, the translation path 300 may be along a chest of the patient in order to acquire images of the patient's lung.

Figure 6:
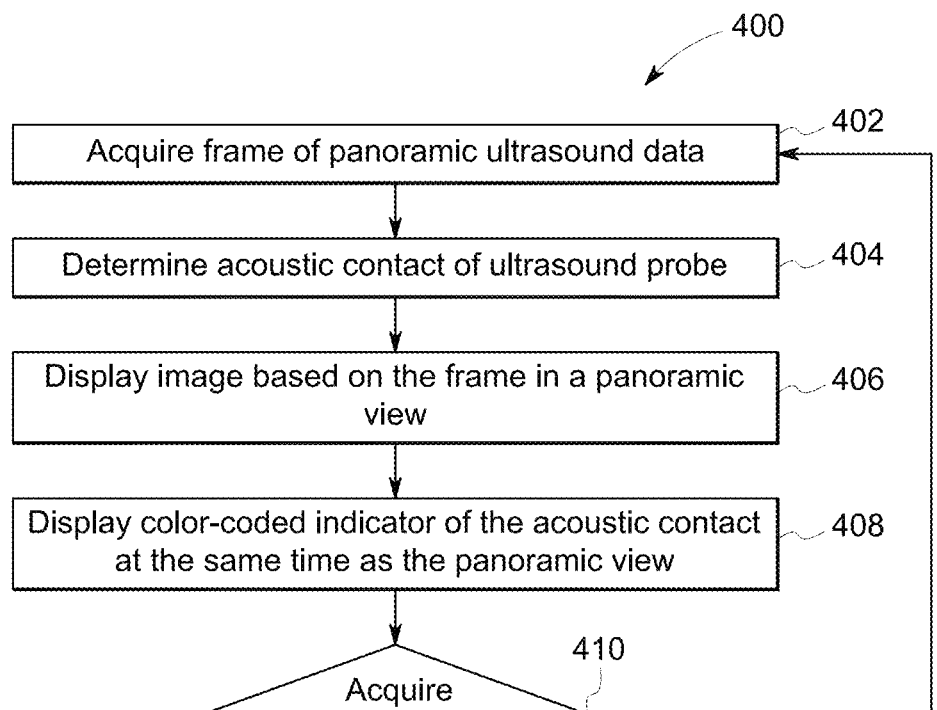
FIG. 6 is a flow chart of a method in accordance with an embodiment.

FIG. 6 illustrates a flowchart of one embodiment of a method 400 for acquiring panoramic ultrasound data and displaying a panoramic view based on the ultrasound image data. The technical effect of the method 400 is the display of a color-coded indicator of acoustic contact, where the color-coded indictor represents the acoustic contact of the ultrasound probe 106 in real-time during the process of acquiring panoramic ultrasound data. The clinician may translate the ultrasound probe 106 in order to acquire panoramic ultrasound data. The method 400 may be performed while translating the ultrasound probe 106 along a translation path, such as the translation path shown in FIG. 5, according to various embodiments.

At step 402, the processor 116 controls the ultrasound probe 106 to acquire a frame of panoramic ultrasound data. The frame of panoramic ultrasound data acquired at step 402 may be acquired while translating the ultrasound probe 106.

Next, at step 404, the processor 116 determines the acoustic contact of the scanning surface 109 of the ultrasound probe 106. The processor 116 may determine the acoustic contact based on intensity levels in the frame of panoramic ultrasound data. According to an embodiment, the processor 116 may determine the acoustic contact based on the intensity levels of the real-time ultrasound data. For example, when the panoramic ultrasound data is B-mode data, the processor 116 may compare the intensity values of the B-mode data to a threshold in order to determine the portions of the scanning surface 109 that have acoustic contact with the patient. The threshold may be a predetermined threshold, or, the threshold may be based on pre-scan data.

According to an embodiment, the processor 116 may use previously acquired panoramic ultrasound data in order to determine the threshold. For example, the processor 116 may use an average intensity determined from one or more frames of previously acquired panoramic ultrasound data and use the average intensity as the threshold. The processor 116 may also use an average intensity from a portion of one or more frames of the previously acquired panoramic ultrasound data to determine the threshold. For example, the threshold may be determined based on the top percentage of the panoramic ultrasound data in a depth direction. The processor 116 may use the only the top 50%, 75%, or any other percentage of the previously acquired panoramic ultrasound data to determine the threshold. Using only a top percentage of the previously acquired panoramic ultrasound data eliminates the data acquired from deeper scan depths, which would, on average, tend to have lower intensity values. The processor 116 may also exclude a portion of the previously acquired panoramic data from the average used to determine the threshold. For example, some or all of the data from the top 2 cm in the depth direction may be excluded from the average in order to minimize the effects of near-field reverberation.

According to an embodiment, the processor 116 may obtain pre-scan ultrasound data prior to the start of the method 400. The pre-scan ultrasound data may be used to determine the values of one or more thresholds that will be used to determine the portions of the transducer array with acoustic contact. The processor 116 may, for example, determine an average intensity based on the pre-scan ultrasound data and use the average intensity to set the threshold. For example, the threshold may be an intensity level that is a fixed amount below or a fixed percentage below the average intensity level in the pre-scan ultrasound data.

According to another embodiment, the processor 116 may determine the threshold based on a portion of the pre-scan ultrasound data. For example, the processor 116 may use only the top percentage, such as the top 50% or the 75% of the pre-scan ultrasound data in the depth direction, and exclude a near-field region that is between 0 cm and 2 cm from the a face of the ultrasound probe.

The processor 116 may build each frame of data by sequentially acquiring data along a plurality of scan lines. The processor 116 may control the ultrasound probe 106 so that only a subset of the transducer elements is active while receiving data along each of the scan lines. In order to acquire high-quality panoramic ultrasound data, it is desirable for each of the transducer elements that are being actively used to have acoustic contact with the object being scanned. If all the elements in the subset have acoustic contact, then it is expected that the average intensity of the data for that particular line will be above the threshold. However, if one or more of the elements in the subset does not have acoustic contact, then the average intensity of the data for that particular line is expected to be below the threshold.

At step 404, based on the intensities of the panoramic ultrasound data from the transducer elements, the processor 116 is able to identify, for each frame, the acoustic contact of the scanning surface 109 of the ultrasound probe 106.

Figure 7:
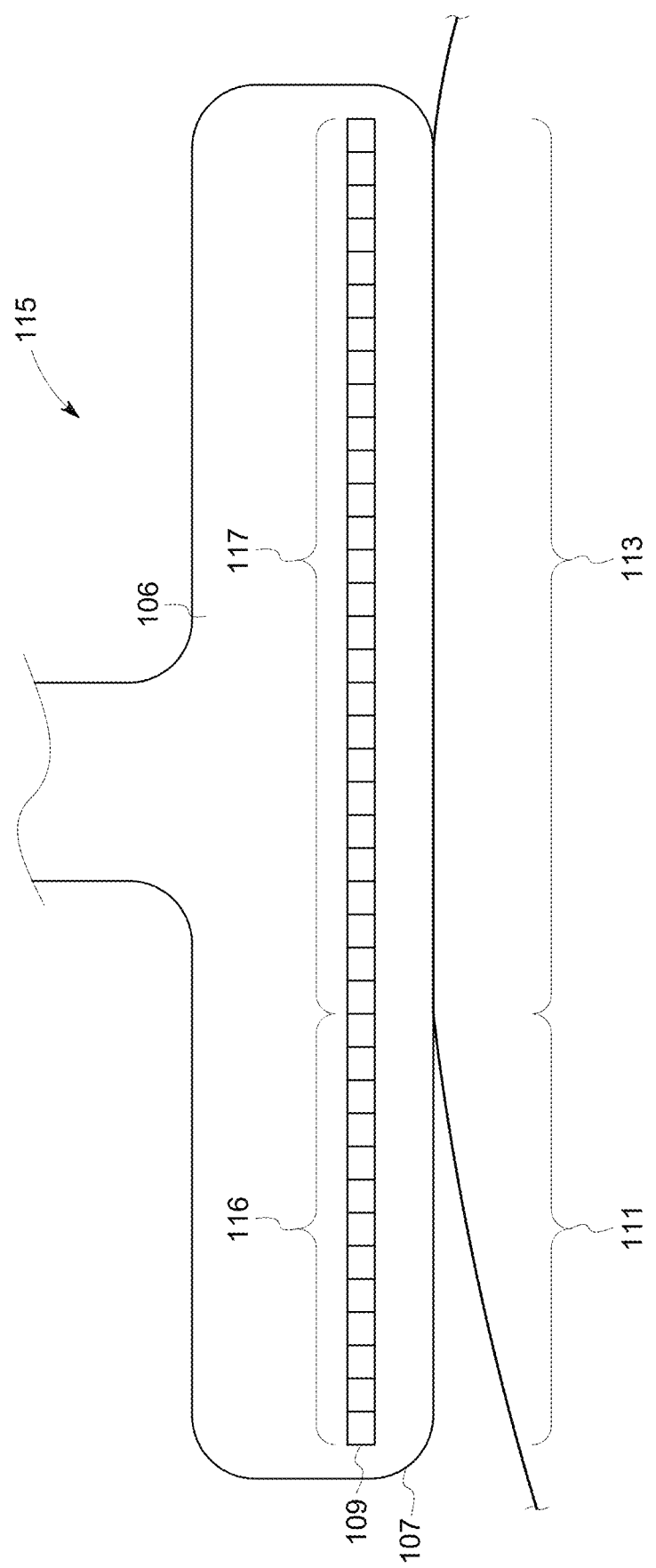
FIG. 7 is a schematic illustration of an ultrasound probe in contact with an object.

FIG. 7 is a schematic representation of the ultrasound probe 106, and the transducer array 109. A first portion 111 of the scanning surface 107 is not in acoustic contact with an object 115 being scanned and a second portion 113 of the scanning surface is not in acoustic contact with the object 115. FIG. 7 indicates a first subset 116 of the transducer elements corresponding to the first portion 111 and a second subset 117 of the transducer elements corresponding to the second portion 113 of the scanning surface 107.

Since the first portion 111 of the scanning surface does not have acoustic contact, it is not possible to receive ultrasonic signals from the corresponding portion of the transducer array—i.e., the first subset 116 of the transducer elements. On the other hand, since the second portion 113 of the scanning surface has acoustic contact, it is possible to receive ultrasonic signals from the corresponding portion of the transducer array—i.e., the second subset 117 of the transducer elements. The signals received from the first subset 116 of transducer elements are expected to have intensities of zero or close to zero. By comparing the intensities of the panoramic ultrasound data acquired from the ultrasound probe 106 in the position shown in FIG. 7, the processor 116 is able to identify that the first portion 111 of the scanning surface 107 does not have acoustic contact with the object 115.

At step 406, to processor 116 displays an image based on the frame of panoramic ultrasound data in an acquisition view.

At step 408, the processor 116 displays a color-coded indicator of the acoustic contact of the ultrasound probe at the same time as the acquisition view. The color-coded indicator will be described in detail hereinafter.

At step 410, the processor 116 determines if it is desired to acquire an additional frame of panoramic ultrasound data. If it is desired to acquire an additional frame of panoramic ultrasound data, the method 400 returns to step 402, where the processor 116 controls the ultrasound probe 106 to acquire an additional frame of panoramic ultrasound data. If, at step 410, it is not desired to acquire an additional frame of panoramic ultrasound data, the method 400 advances to step 412.

Figure 8:
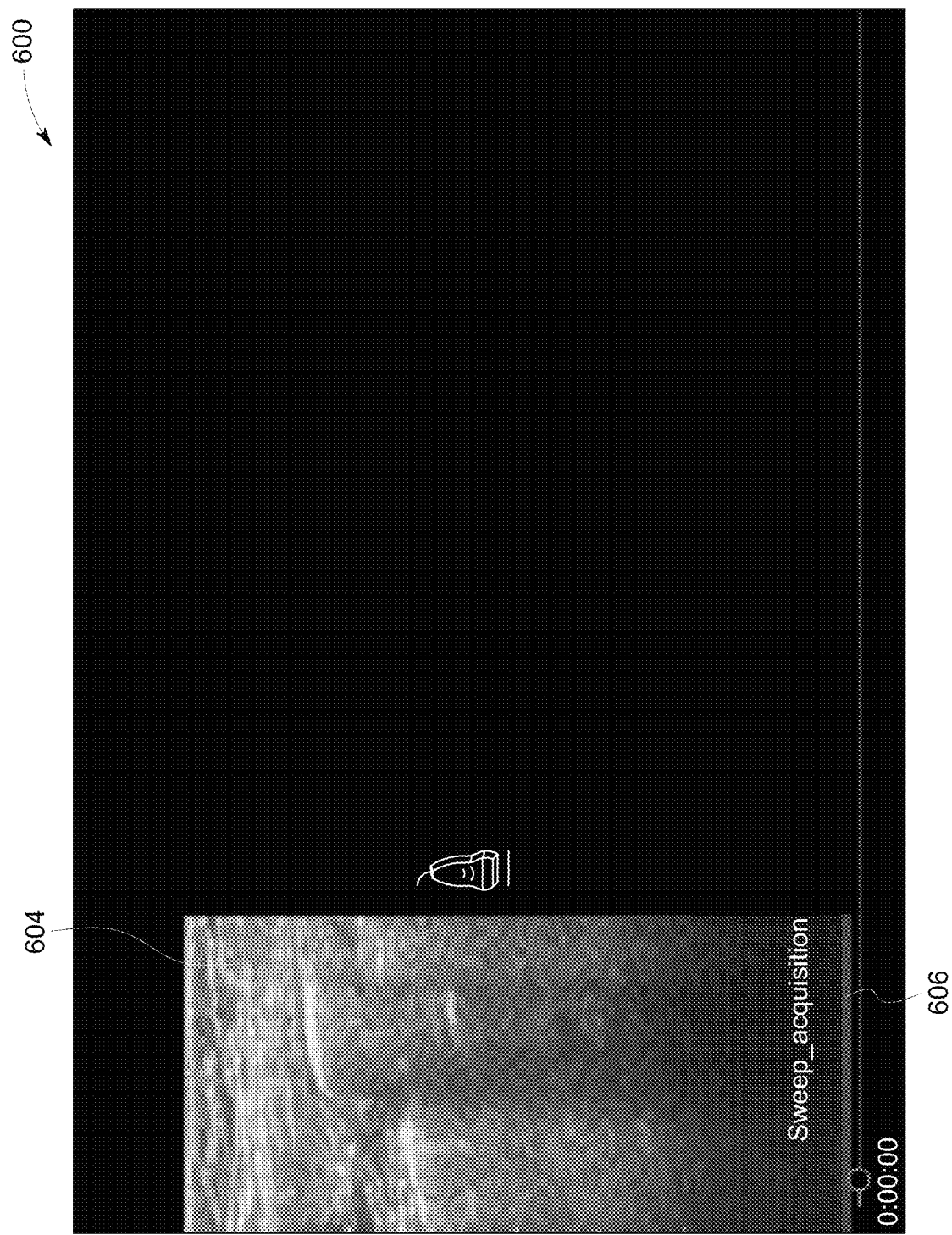
FIG. 8 is an acquisition view according to an embodiment.
Figure 9:
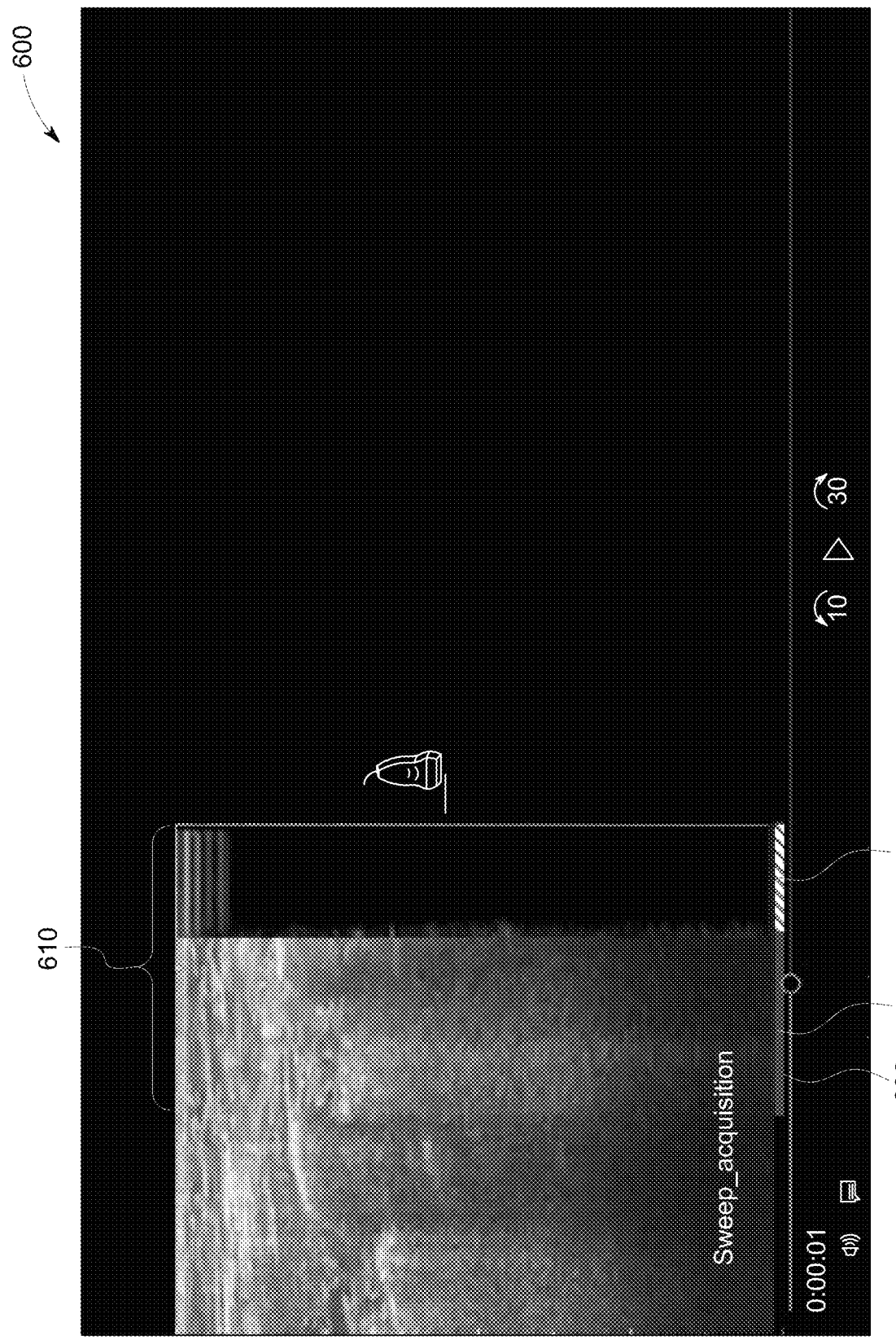
FIG. 9 is an acquisition view according to an embodiment.
Figure 10:
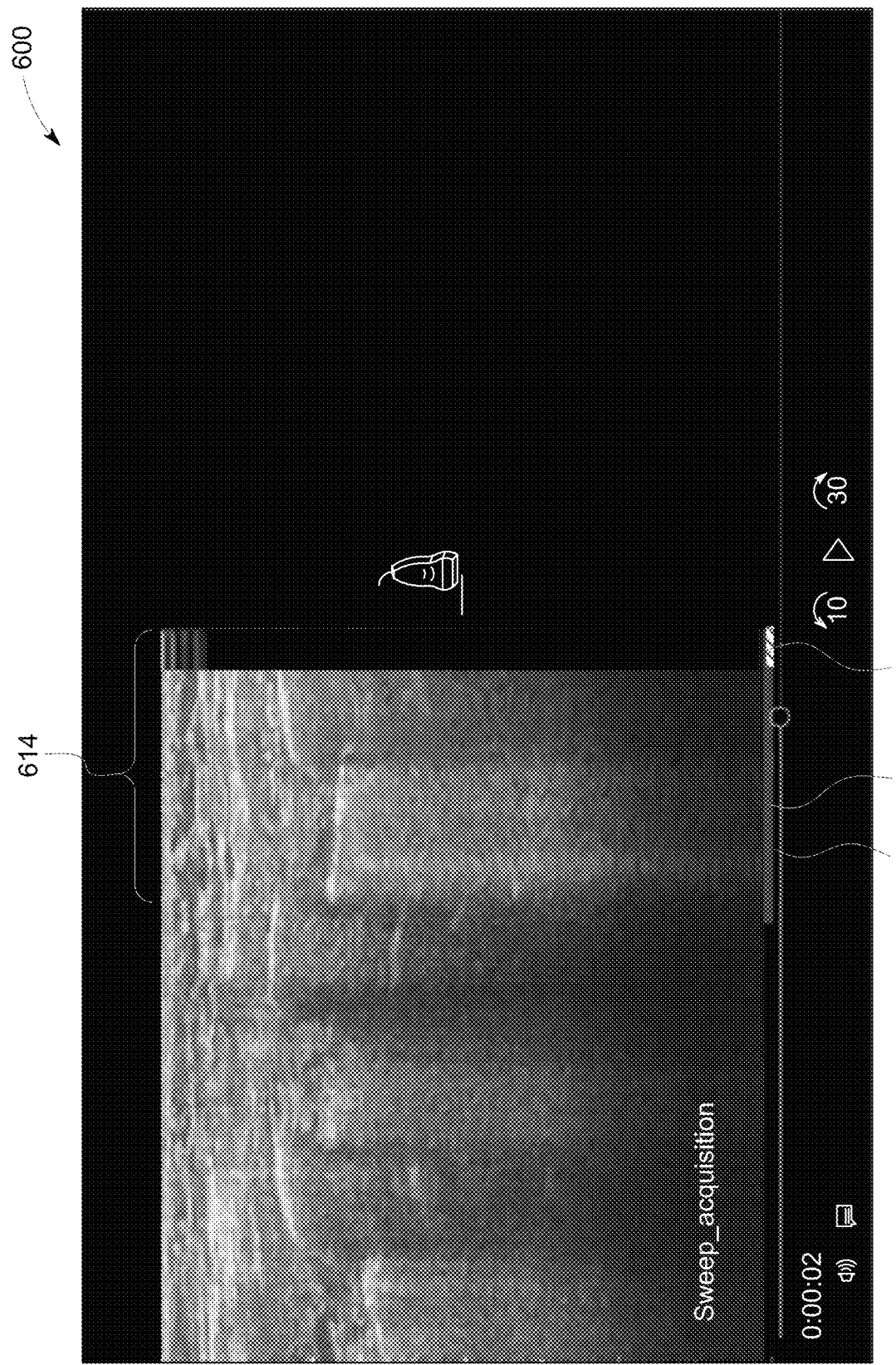
FIG. 10 is an acquisition view according to an embodiment.
Figure 11:
FIG. 11 is an acquisition view according to an embodiment.
Figure 12:
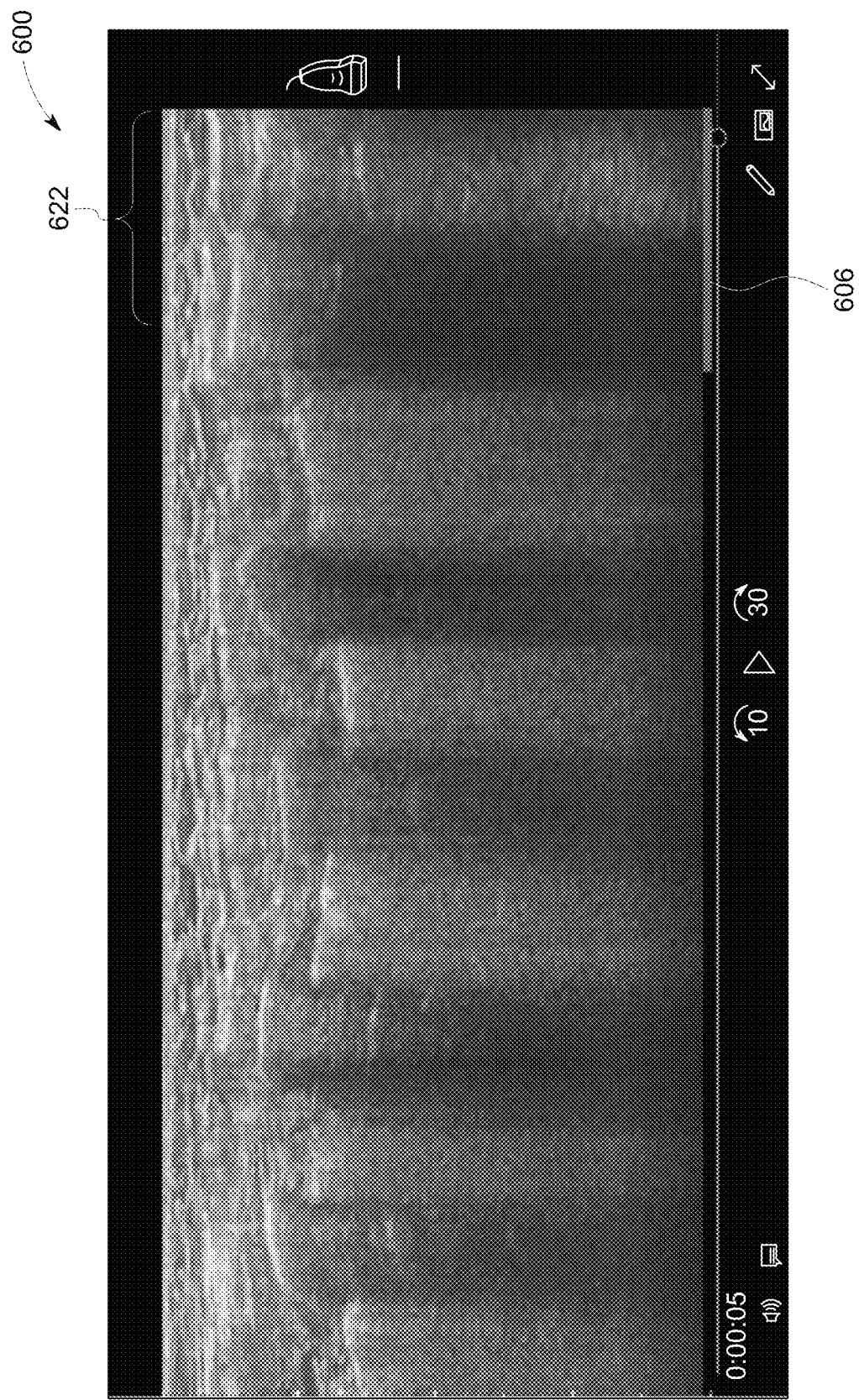
FIG. 12 is an acquisition view according to an embodiment.

FIG. 8 is an acquisition view 600 at time T1; FIG. 9 is the acquisition view 600 at time T2; FIG. 10 is the acquisition view 600 at time T3; FIG. 11 is the acquisition view 600 at time T4, and FIG. 12 represents the acquisition view 600 at time T5.

Typically, during the acquisition of panoramic ultrasound data, the user translates the ultrasound probe 106 along a translation path, such as the translation path 300 shown in FIG. 5. FIGS. 5, 6, 7, 8, 9, and 10 will be used in order to describe how an acquisition view may be built-up and displayed using the method 400 according to an exemplary embodiment.

For example, a first iteration through steps 402, 404, 406, 408 and 410 will result in the display of a frame 604 in the acquisition view 600, at time T1 as shown in in FIG. 5. The acquisition view 600 shown in FIG. 8 only shows the frame 604 acquired at time T1 from position P1. Frame 604 represents the live image at the time T1. FIG. 8 includes a color-coded indicator 606 that is displayed at the same time as the panoramic view 600. The color-coded indicator 606 represents the acoustic contact of the scanning surface 107 of the ultrasound probe 106 at time T1 when the frame 604 was acquired. Additional details about the calculation of the acoustic contact will be discussed hereinafter. Each additional iteration of the steps 402, 404, 406, 408 and 410 will result in the display of an additional frame representing the most recently-acquired panoramic ultrasound data. The color-coded indicator 606 is updated in real-time in order to reflect the acoustic contact of the scanning surface 107 during the most recently-acquired frame of panoramic ultrasound data. The color of the color-coded indicator 606 will therefore be adjusted in real-time as additional panoramic ultrasound data is acquired in order to always reflect the acoustic contact of the scanning surface 107 in real-time.

As the clinician translates the ultrasound probe 106 along the translation path 300, the processor iteratively repeats steps 402, 404, 406, 408 and 410. For example, at time T2 the processor 116 controls the ultrasound probe 106 to acquire an additional frame of panoramic ultrasound data. FIG. 9 represents the acquisition view 600 at the time T2. FIG. 9 includes the color-coded indicator 606 representing the acoustic contract at the time T2 when image frame 610 was acquired. The processor 116 continues to iteratively repeat steps 402, 404, 406, 408 and 410 of the method 400 in order to acquire additional frames of panoramic ultrasound data. FIG. 10 represents the acquisition view 600 at the time T3 and includes the color-coded indicator 606 representing the acoustic contact at the time T3 when the image frame 614 was acquired. FIG. 11 represents the acquisition view 600 at the time T4, and FIG. 10 represents the panoramic view 600 at the time T5. FIG. 11 includes the color-coded-indicator 606 representing the acoustic contact at the time T4 when image frame 618 was acquired. FIG. 12 includes the color-coded indicator 606 at time T5 when the image frame 622 was acquired.

In FIG. 8, the color-coded indicator 606 is all a first color to indicate that all of the scanning surface 107 of the ultrasound probe 106 has acoustic contact with the object being scanned at time T1. According to an embodiment, the first color may be green to indicate acoustic contact, but any other color may be used to indicate acoustic contact. In FIG. 9, the color-coded indicator 606 includes a first color, used to indicate a first portion of the scanning surface 107 with acoustic contact and a second color, used to indicator a second portion of the scanning surface without acoustic contact at time T2. A first portion 607 of the color-coded indicator is shown in the first color and a second portion 609 of the color-coded indicator is shown in the second color in FIG. 9. The hatching ("///") is used to indicate the second color in FIG. 9. According to an embodiment, the second color may be yellow, although any other color may be used on the color-coded indicator to indicate the second portion of the scanning surface without acoustic contact. In FIG. 10, the second portion 609 of the color-coded indicator is smaller than in FIG. 9. This indicates that more of the scanning surface 107 has acoustic contact at time T3 (shown in FIG. 10) compared to time T2 (shown in FIG. 9).

In FIG. 11, representing time T4, the color-coded indicator 606 includes the first portion 607 and the second portion 609. However, the second portion 609 is shown in a third color as indicated by the back-hatching ("\\\\"). According to an embodiment, the third color may be used indicate the percentage of the scanning surface 107 without acoustic contact exceeds a threshold. According to the embodiment shown in FIGS. 8, 9, 10, 11, and 12, the threshold may be 50% of the scanning surface 107. At time T3, represented in FIG. 11, more than 50% of the scanning surface 107 is without acoustic contact. As such, the second portion 609 of the color-coded indicator is shown in the third color to indicate to the user that the percentage of the scanning surface 107 without acoustic contact exceeds a threshold. The third color may be red, but the third color may any other color according to various embodiments. Changing the color used to illustrate the second portion 609 of the color-coded indicator 606 when the percentage of the scanning surface 107 without acoustic contact exceeds a threshold provides a clear visual signal to the clinician that the acoustic contact of the scanning surface 107 is decreasing.

In FIG. 12, representing time T5, the color-coded indicator 606 is shown as a single color to indicate that 100% of the scanning surface 107 is in contact with the object being scanned.

In the embodiment shown in FIGS. 8, 9, 10, 11, and 12, the color-coded indicator 606 is horizontally aligned with the live image. In other words, the portion of the acquisition view 600 above the color-coded indicator 606 is the live image based on the real-time panoramic ultrasound data. The color-coded indicator 606 is shown at the bottom of the live image in FIGS. 8, 9, 10, 11, and 12, but the color-coded indicator 606 may be positioned anywhere on the display device 118 according to various embodiments.

As steps 402, 404, 406, 408 and 410 of the method 400 are iteratively repeated, the live image is always displayed on the right-hand side of the acquisition view 600. The live image is based on real-time panoramic ultrasound data acquired from the current position of the ultrasound probe 106. The acquisition view 600 may show both the live image and images generated from previously acquired panoramic ultrasound data. In the acquisition view 600, the previously acquired panoramic ultrasound data may be represented as still images. For example, in FIGS. 8, 9, 10, 11, and 12, the acquisition view 600 includes a live image at the right side of the acquisition view and the portion to the left of the live image is represented as one or more still images according to an embodiment.

By displaying the most recently acquired frame of panoramic ultrasound data in the acquisition view, the processor 116 displays a live image reflecting the real-time ultrasound data acquired from the current position of the ultrasound probe 106.

Referring to step 412, of the method 400, the processor 116 is configured to identify a first subset of the panoramic ultrasound data that was acquired with acoustic contact and a second subset of the panoramic ultrasound data that was acquired without acoustic contact. According to an embodiment, the processor may use only the first subset of the panoramic ultrasound data to generate a panoramic view including a plurality of videos.

Figure 13:
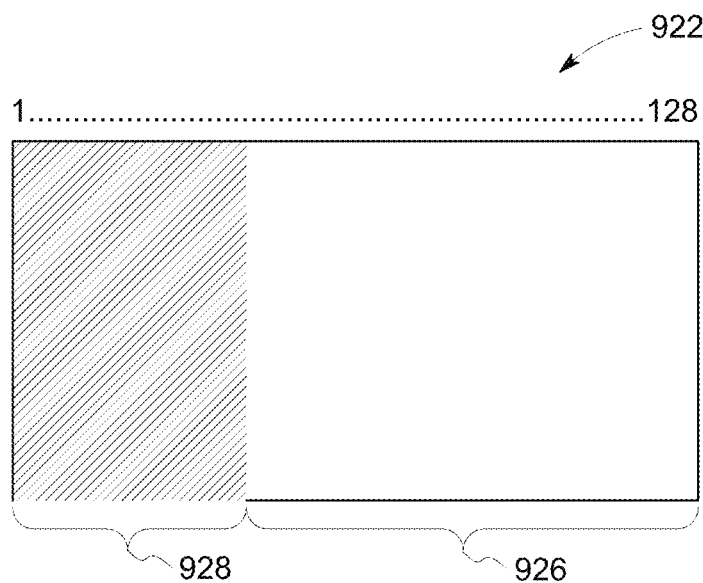
FIG. 13 is a schematic representation of a frame of panoramic ultrasound data according to an embodiment.

Based on the information about the acoustic contact, at step 412, the processor 116 identifies a first subset of the panoramic ultrasound data acquired with acoustic contact. During the method 400, the processor 116 determines the acoustic contact of the scanning surface 107 of the ultrasound probe 106 at step 404 for each image frame of panoramic ultrasound data. FIG. 13 represents an image frame 922 of panoramic ultrasound data acquired as part of the method 400. The transducer elements 1-128 are shown across the top of the image frame 922. According to an embodiment, the frame 922 is generated based on the frame of panoramic ultrasound data acquired with the ultrasound probe 106 in the position represented in FIG. 7. The frame 922 includes a first portion 926 and a second portion 928. The first portion 926 was acquired while the scanning surface 107 had acoustic contact and the second portion 928 was acquired while the scanning surface 107 did not have acoustic contact. At step 412, the processor 116 identifies a first subset of the panoramic data acquired with acoustic contact. The subset of the panoramic ultrasound data used to generate the first portion 926 of the frame would be part of the first subset of the panoramic ultrasound data and the subset of the panoramic ultrasound data used to generate the second portion 928 would be part of the second subset of the panoramic ultrasound data. At step 412, the processor 116 determines, for each of the image frames acquired as part of the method 400, the portion of the data that was acquired with acoustic contact and the portion of the data that was acquired without acoustic contact. The first subset of the panoramic ultrasound data acquired with acoustic contact represents the portions of all of the frames that were acquired with acoustic contact. The second subset of the panoramic ultrasound data acquired without acoustic contact represents the portions of all the frames that were acquired without acoustic contact.

Figure 14:
FIG. 14 illustrates one example of ultrasound image data of a lung and ribs.
Figure 15:
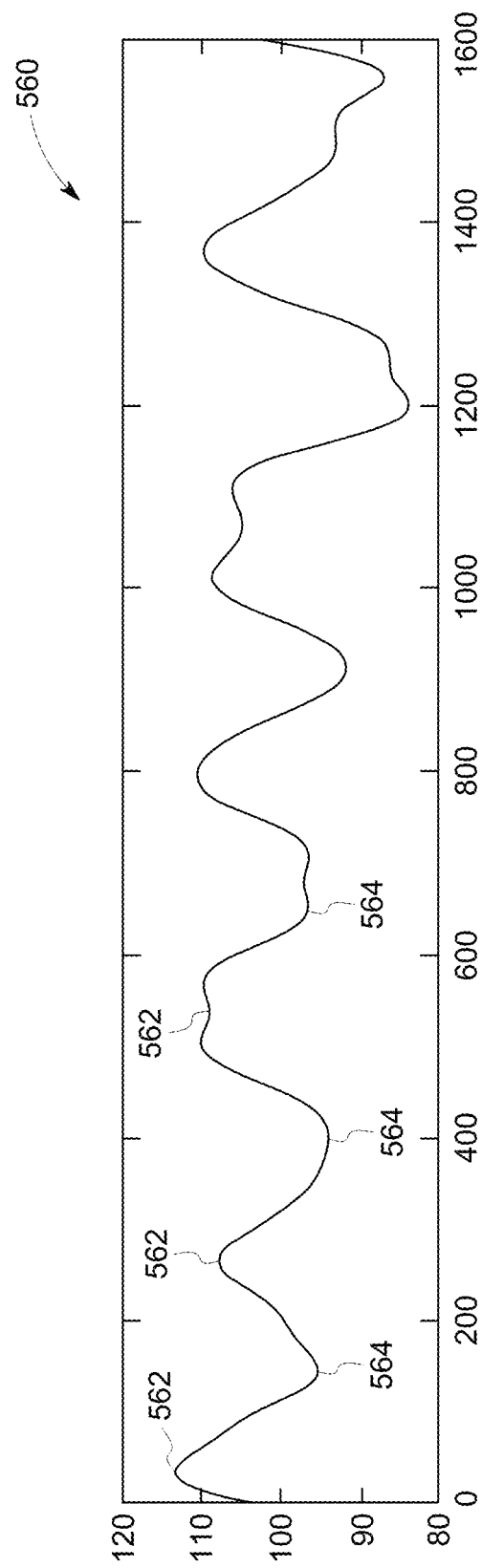
FIG. 15 is a plot of Center-of-Mass versus time according to an embodiment.
Figure 16:
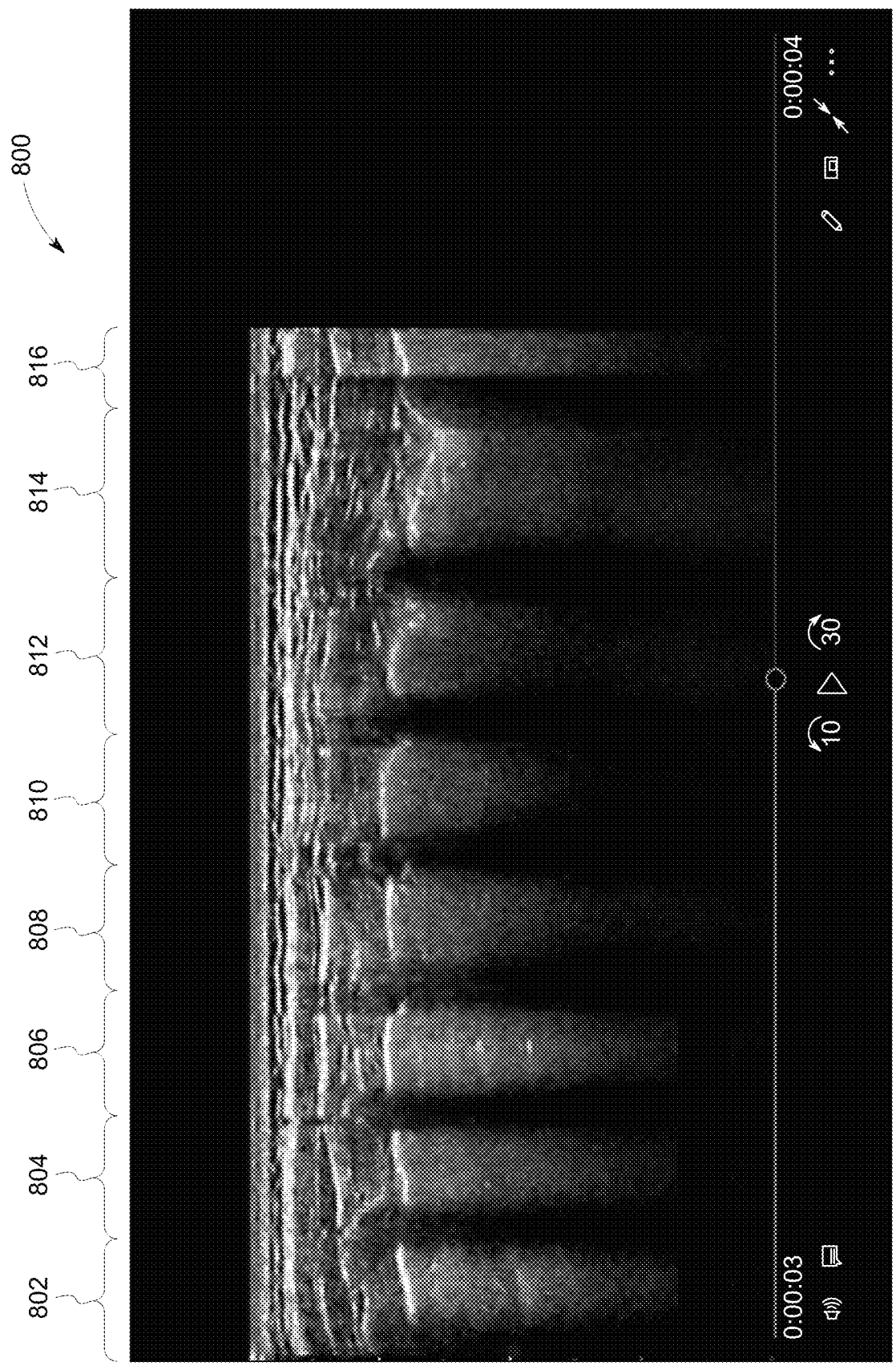
FIG. 16 is an illustration of a panoramic view according to an embodiment.

At step 414, the processor 116 generates a panoramic view including a plurality of videos from the first subset of the panoramic ultrasound data. According to an exemplary embodiment, the panoramic view may be based on panoramic ultrasound data acquired of the patient's chest. FIGS. 14, 15, and 16 will be used to help describe an exemplary embodiment.

FIG. 14 illustrates one example of panoramic ultrasound image data 500 of the lung 208 and ribs of the person 204 acquired with the ultrasound probe 106 held in a sagittal orientation. FIG. 14 includes a plurality of segments of interest and a plurality of rib shadows. Each of the segments of interest is an intercostal space between the patient's ribs. The rib shadows indicate locations where passage of the pulsed ultrasonic signals was blocked by the ribs. For example, FIG. 14 includes a first segment of interest 531, a second segment of interest 532, a third segment of interest 533, and a fourth segment of interest 534. FIG. 14 also includes a second rib shadow 522, a third rib shadow 523, and a fourth rib shadow 524. The second rib shadow 522 is caused by the second rib 222; the third rib shadow 523 is caused by the third rib 223; and the fourth rib shadow 524 is caused by the fourth rib 224.

In one embodiment, the processor 116 may be configured to automatically identify segments of interest in the ultrasound image data. A segment of interest can be a subset or portion of the panoramic image data that is selected based on characteristics of the image data. The processor 116 can examine characteristics of the pixels (or other subsets of the image data) to identify the segments of interest, such as the color, intensity, brightness, or the like, of the pixels in the image data.

The processor 116 can examine the image data acquired by the ultrasound probe 106 to determine how quickly the probe 106 is moving relative to the body of the person 204. For example, as new or additional panoramic ultrasound image data is acquired of new or different areas of the lung 208, ribs, or the like, the processor 116 can determine that the ultrasound probe 106 is being moved. These new or different areas can include image data of additional intercostal spaces and/or rib shadows. The processor 116 identifies segments of interest in the panoramic ultrasound data. According to an exemplary embodiment, it may be desirable to identify segments of interest corresponding to the intercostal spaces, such as the first intercostal space 231, the second intercostal space 232, the third intercostal space 233, the fourth intercostal space 234, and the fifth intercostal space 235. The processor 116 can identify the segments of interest, such as the intercostal spaces, based on changes in the characteristics of the image data, such as changes in intensity (e.g., brighter in intensity when an intercostal space is being imaged or lower in brightness when a rib is being imaged). An exemplary embodiment showing how the processor 116 may use intensity information in the ultrasound image data to identify the segments of interest will be described with respect to FIG. 14.

According to an embodiment, the processor 116 may identify the segments of interest based on the intensity of the ultrasound image data. For example, the processor 116 may compare the ultrasound image data to a threshold: if the ultrasound image data is above a threshold, the ultrasound image data is of a segment of interest; if the ultrasound image data is below the threshold, the ultrasound image data represents a rib shadow and does not include a segment of interest. According to embodiments, the processor 116 may use other image properties to identify the segments of interest from the ultrasound image data. For example, the processor 116 may use information such as Doppler data, speckle tracking, or colorflow data to identify the segments of interest within the ultrasound image data. The processor 116 may also use artificial intelligence, such as by using a neural network to identify the segments of interest in the ultrasound image data.

According to another embodiment, the processor 116 may use a center-of-mass (COM) calculation where pixel intensity in the image is treated as the equivalent of mass. The processor 116 may calculate the vertical position of the COM at each location in the direction of the translation or sweep of the ultrasound probe 106. At locations where there is a rib and a rib shadow, the COM tends to be close to the surface of the ultrasound probe 106 (i.e., at shallower depths in the image), while the COM tends to be deeper for portions of the image with an intercostal space. The processor 116 may determine the positions of rib shadows and intercostal spaces based on the COM calculation with respect to either time or distance. For example, according to an exemplary embodiment, the processor 116 may identify positions of ribs and rib shadow by identifying regions of the image where the COM calculation is relatively high; and the processor 116 may identify positions of intercostal spaces or pleural regions in the image by identifying regions of the image where the COM calculations are relatively low. For example, FIG. 15 shows an example of a COM plot 560. The COM plot 560 shows the vertical position of the COM with respect to horizontal position in the image. The processor 116 may identify the relative peaks 562 in the COM plot 560 and the relative valleys 564 in the COM plot 560. The relative peaks 562 correspond to regions of the image with ribs and rib shadows whereas the relative valleys 564 correspond to regions of the image obtains from intercostal spaces/pleural regions.

At step 414, the processor generates a panoramic view based on the first subset of panoramic ultrasound data identified at step 412. The processor 116 may, for instance, analyze the ultrasound data to see if one or more segments of interest were acquired with acoustic contact. The processor 116 may perform this analysis on each frame of data. The processor may use information about the intensity of the panoramic ultrasound data or the center-of-mass as described previously in order to determine if the intercostal space represented in the frame was acquired with acoustic contact. If the intercostal space, or a different segment of interest, in the frame was acquired with acoustic contact, then the processor 116 may segment just the portion of the frame with acoustic contact and use it to generate the panoramic view. If only a portion of the segment of interest was acquired with acoustic contact, then the processor 116 may discard the frame. Some frames that were acquired may include multiple intercostal spaces. For theses frames, the processor 116 may only select to use a subset of the multiple intercostal spaces that were acquired with acoustic contact for the panoramic view. In this manner, the processor 116 only uses the first subset of panoramic ultrasound data acquired with acoustic contact to generate the panoramic view.

FIG. 16 is an illustration of a panoramic view 800 according to an embodiment. As described previously, a panoramic view 800 can be acquired by obtaining different portions of the ultrasound image data as the probe 106 is moved over the person 204, and then stitching or otherwise combining these different ultrasound image data portions together to form the panoramic view. The processor 116 may use image information, such as brightness values, shape/pattern identification, or other matching algorithms to combine the portions of the ultrasound image data associated with various segments of interest in the panoramic view 800.

The panoramic view 800 of the ultrasound image data can show or include more image data of the patient than the ultrasound probe 106 can obtain in a single field-of-view (FOV). For example, the FOV of the ultrasound probe 106 may be much smaller than the panoramic view 800.

Referring to FIG. 16, the panoramic view 800 includes a first portion 802, a second portion 804, a third portion 806, a fourth portion 808, a fifth portion 810, a sixth portion 812, a seventh portion 814, and an eighth portion 816. A video based on a different segment of interest is displayed in each of the portions of the panoramic view 800. For example, a first video based on a first segment of interest may be displayed in the first portion 802; a second video based on a second segment of interest may be displayed in the second portion 804; a third video based on a third segment of interest may be displayed in the third portion 806; a fourth video based on a fourth segment of interest may be displayed in the fourth portion 808; a fifth video based on a fifth segment of interest may be displayed in the fifth portion 810; a sixth video based on a sixth segment of interest may be displayed in the sixth portion 812; a seventh video based on a seventh segment of interest may be displayed in the seventh portion 814; and an eighth video based on an eight segment of interest may be shown in the eighth portion 816. According to the embodiment shown in FIG. 16, each of the segments of interest may be ultrasound image data acquired from a different intercostal space of a patient's lung region.

According to an embodiment, displaying each of the plurality of videos in the panoramic view may include displaying each of the plurality of videos as a repeating loop, or cine loop. When displayed as a repeating loop, each video is continuously replayed. In other words, each video transitions from the last frame in the video to the first frame in video when displayed as a repeating loop. Temporally scaling the ultrasound image data refers to adjusting the length of time it takes each video to play before looping or repeating. The length of time it takes for each video to play in a panoramic view may also be referred to as a period of the repeating loop. Temporally scaling may be used so that each of the videos displayed as a repeating loop in the panoramic view has the same period.

According to an embodiment, the processor 116 may automatically abort the acquisition of the panoramic ultrasound data in response to determining that the acoustic contact has dropped below a cutoff threshold. For example, the processor 116 may automatically freeze the ultrasound probe 106 in response to detecting the acoustic contact of the scanning surface 107 is less than a cutoff threshold. According to an embodiment, the cutoff threshold may be a predetermined value, or the cutoff threshold may be determined based on pre-scan ultrasound data acquired before the starting the method 400. For instance, the processor 116 may automatically freeze the ultrasound probe 106 is less than a certain percentage of the transducer array has acceptable acoustic contact.

Displaying the color-coded indicator of the acoustic contact during the acquisition of panoramic ultrasound data provides real-time feedback to the clinician during the acquisition of panoramic ultrasound data. The clinician can use this real-time feedback to make small corrections or adjustments to the orientation of the ultrasound probe 106 with respect to the patient and/or the pressure being used to hold the ultrasound probe 106 against the patient. Acquiring enough panoramic ultrasound data to generate a panoramic video can be a relatively time-consuming procedure since the clinician needs to slowly translate the ultrasound probe 106 along the desired translation path. If the acoustic contact is poor it may be necessary to repeat the entire acquisition. Providing real-time feedback about acoustic contact through the color-coded indicator helps the clinician to acquire panoramic ultrasound data with acoustic contact on the first attempt, thus saving time and enhancing the patient experience.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of ultrasound imaging, said method comprising:
   acquiring panoramic ultrasound data of an object while translating an ultrasound probe, wherein the ultrasound probe includes a scanning surface;
   displaying an acquisition view during the process of acquiring the panoramic ultrasound data, wherein the acquisition view comprises a live image representing real-time ultrasound data acquired from a current position of the ultrasound probe and one or more still images displayed to the left of the live image, the one or more still images representing previously acquired panoramic ultrasound data, wherein a position of the live image is moved to the right with respect to the acquisition view during the process of acquiring the panoramic ultrasound data;
   automatically determining acoustic contact of the scanning surface with the object while acquiring the panoramic ultrasound data;
   displaying a color-coded indicator at the same time as the acquisition view, wherein the color-coded indicator represents the acoustic contact of the scanning surface in real-time during the process of acquiring the panoramic ultrasound data and comprises a bar extending an entire width of the live image and directly contacting a bottom edge of the live image, wherein the bottom edge is at an opposite side of the live image with respect to the ultrasound probe,
   wherein the color-coded indicator is horizontally aligned with the live image during the process of acquiring the panoramic ultrasound data, and wherein the color-coded indicator is moved to the right during the process of acquiring the panoramic ultrasound data so that the color-coded indicator remains horizontally aligned with the live image as the live image is moved during the process of acquiring the panoramic ultrasound data;
   wherein a length of the bar is color-coded such that the bar is displayed in a first color to indicate acoustic contact of the scanning surface in response to determining that the entire scanning surface has acoustic contact, the bar is displayed in a second color that is different from the first color to indicate that the scanning surface does not have acoustic contact in response to determining that entire scanning surface does not have acoustic contact, and a first portion of the bar is displayed in the first color to indicate acoustic contact for a corresponding first portion of the scanning surface and a second portion of the bar is displayed in the second color to indicate that a corresponding second portion of the scanning surface does not have acoustic contact in response to determining the first portion of the scanning surface has acoustic contact and the second portion of the scanning surface does not have acoustic contact.

2. The method of claim 1, wherein said determining the acoustic contact of the scanning surface comprises comparing intensities of the panoramic ultrasound data to a threshold.

3. The method of claim 1, wherein the first color is green and the second color is red.

4. The method of claim 1, further comprising: identifying a first subset of the panoramic ultrasound data that was acquired with acoustic contact and a second subset of the panoramic ultrasound data that was acquired without acoustic contact; and generating a panoramic view comprising a plurality of videos based on the first subset of the panoramic ultrasound data, wherein the panoramic view does not include the second subset of the panoramic ultrasound data.

5. The method of claim 2, wherein the threshold is determined based on the panoramic ultrasound data.

6. The method of claim 2, wherein the threshold is determined based on a pre-scan ultrasound data of the object.

7. The method of claim 4, wherein the panoramic ultrasound data was acquired from a lung and includes a plurality of intercostal spaces, and wherein the plurality of intercostal spaces are represented by the plurality of videos.

8. The method of claim 7, wherein the panoramic ultrasound data includes a plurality of frames of ultrasound data, and wherein a first portion of one of the frames is in is in the first subset and a second portion of the frame is in the second subset.

9. The method of claim 7, wherein the panoramic ultrasound data includes a plurality of frames of ultrasound data, and wherein the plurality of videos in the panoramic view are generated based on one or more of the plurality of frames of ultrasound data, portions of one or more of the plurality of frames with acoustic contact, or both one or more of the plurality of frames of ultrasound data and portions of one or more of the plurality of frames of ultrasound data with acoustic contact.

10. An ultrasound imaging system comprising:
a display device;
an ultrasound probe including a scanning surface;
and a processor in electronic communication with the ultrasound probe and the display device, wherein the processor is configured to:
control the ultrasound probe to acquire panoramic ultrasound data of an object while the ultrasound probe is translated;
display an acquisition view on the display device while the ultrasound probe is acquiring the panoramic ultrasound data, wherein the acquisition view comprises a live image representing real-time ultrasound data acquired from a current position of the ultrasound probe and one or more still images displayed to the left of the live image, the one or more still images representing previously acquired panoramic ultrasound data, wherein a position of the live image is moved to the right with respect to the acquisition view during the process of acquiring the panoramic ultrasound data;
display a color-coded indicator at a same time as the acquisition view, wherein the color-coded indicator represents an acoustic contact of the scanning surface in real-time while acquiring the panoramic ultrasound data and comprises a bar extending an entire width of the live image and directly contacting a bottom edge of the live image, wherein a length of the bar is color-coded, wherein the bottom edge is at an opposite side of the live image with respect to the ultrasound probe, wherein the color-coded indicator is horizontally aligned with the live image during the process of acquiring the panoramic ultrasound data, and wherein the color-coded indicator is moved to the right during the process of acquiring the panoramic ultrasound data so that the color-coded indicator remains horizontally aligned on the live image as the live image is moved during the process of acquiring the panoramic ultrasound data;
and display the bar in a first color to indicate acoustic contact of the scanning surface in response to determining that the entire scanning surface has acoustic contact; display the bar in a second color that is different than the first color to indicate that the scanning surface does not have acoustic contact in response to determining that the entire scanning surface does not have acoustic contact; and display a first portion of the bar in the first color to indicate acoustic contact for a corresponding first portion of the scanning surface and display a second portion of the bar in the second color to indicate that a corresponding second portion of the scanning surface does not have acoustic contact in response to determining the first portion of the scanning surface has acoustic contact and the second portion of the scanning surface does not have acoustic contact.

11. The ultrasound imaging system of claim 10, wherein the processor is configured to adjust the color-coded indicator in real-time as the acoustic contact of the scanning surface changes.

12. The ultrasound imaging system of claim 10, wherein the processor is further configured to: identify a first subset of the panoramic ultrasound data that was acquired with acoustic contact and a second subset of the panoramic ultrasound data that was acquired without acoustic contact; and generate a panoramic view comprising a plurality of videos based on the first subset of the panoramic ultrasound data, wherein the panoramic view does not include the second subset of the panoramic ultrasound data.

13. The ultrasound imaging system of claim 12, wherein the panoramic ultrasound data comprises a plurality of frames, and wherein the first subset includes a first portion of one of the frames and the second subset includes a second portion of the one of the frames.

* * * * *